(12) United States Patent
Samuelsson et al.

(10) Patent No.: US 6,482,193 B1
(45) Date of Patent: Nov. 19, 2002

(54) ABSORBENT ARTICLE WITH A RAISED PORTION

(75) Inventors: Ann Samuelsson, Lindome (SE); Charlotte Persson, Göteborg (SE); Pascale Cabelduc, Göteborg (SE); Solgun Drevik, Mölnlycke (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/647,059
(22) PCT Filed: Mar. 19, 1999
(86) PCT No.: PCT/SE99/00433
§ 371 (c)(1), (2), (4) Date: Sep. 26, 2000
(87) PCT Pub. No.: WO99/48451
PCT Pub. Date: Sep. 30, 1999

(30) Foreign Application Priority Data

Mar. 26, 1998 (SE) .................................................. 9801020

(51) Int. Cl.⁷ .................................................. A61F 13/15
(52) U.S. Cl. .................. 604/385.17; 604/380
(58) Field of Search ................................ 604/379, 380, 604/385.17, 385.18, 378

(56) References Cited

U.S. PATENT DOCUMENTS

| 2,952,259 A | * | 9/1960 | Burgeni |
| 2,952,260 A | * | 9/1960 | Burgeni |
| 4,676,786 A | * | 6/1987 | Nishino |
| 4,758,240 A | | 7/1988 | Glassman |
| 4,936,839 A | * | 6/1990 | Molee et al. |
| 5,423,786 A | * | 6/1995 | Fung et al. |
| 5,558,656 A | | 9/1996 | Bergman |

FOREIGN PATENT DOCUMENTS

| EP | 0 804 917 | 11/1997 |
| WO | WO 90/14063 | 11/1990 |
| WO | WO 94/10953 | 5/1994 |
| WO | WO 94/10956 | 5/1994 |
| WO | WO 98/22059 | 5/1998 |
| WO | wo 98/22062 | 5/1998 |

* cited by examiner

Primary Examiner—Dennis Ruhl
(74) Attorney, Agent, or Firm—Young & Thompson

(57) ABSTRACT

An absorbent article intended for female users, has such a form and size that it can principally be accommodated in the crotch part of a pair of underpants, a longitudinal direction, a transverse direction and a thickness direction. The article displays a liquid-permeable surface (2), and a liquid-impermeable surface (3), and also an absorbent core consisting of at least one absorbent body (5) arranged between the two surfaces (2, 3). A raised portion (7) extending in the longitudinal direction and displaying two end portions is arranged at the liquid-permeable surface (2) of the article. The raised portion (5) displays spacing elements (16) which during use of the article create channels (17) for the flow of liquid between the raised portion (5) and the body of the user.

11 Claims, 3 Drawing Sheets

ABSORBENT ARTICLE WITH A RAISED PORTION

TECHNICAL FIELD

The invention relates to an absorbent article intended for female users, such as a sanitary napkin or an incontinence protector, having such a form and size that it can principally be accommodated in the crotch part of a pair of underpants and having a longitudinal direction, a transverse direction and a thickness direction, wherein the article displays a liquid-permeable surface, and a liquid-impermeable surface, and also an absorbent core consisting of at least one absorbent body arranged between the two surfaces, and wherein a raised portion extending in the longitudinal direction is arranged at the liquid-permeable surface of the article.

BACKGROUND

A common problem associated with absorbent articles of the type intended here is leakage of body fluid out beyond the longitudinal side edges of the article. Such leakage is naturally extremely undesirable since it involves a risk of soiling the clothes of the user. Due to the rather inconsiderable extension of the article even in the longitudinal direction, it is, moreover, not unusual for liquid to leak out forward or backwards beyond the end edges of the article.

A common reason for edge leakage is that the absorbent article is deformed during use when the article is compressed between the thighs of the user. This leads to pleating in both the absorbent core of the article and in its cover material. Such pleating leads to channels being formed in an uncontrolled manner on the surface of the article, in which channel body fluid can run out beyond the side edge. Moreover, the compression of the article results in a reduction in the surface available for liquid acquisition, leading to a significant risk of body fluid ending up beside the article.

A further problem in connection with the previously known absorbent articles is that the side edges of the article, under the influence of the physical forces which arise when the user moves, are at risk of being folded in over the liquid-permeable surface of the article. Such inward folding also leads to a drastic reduction in the surface available for liquid acquisition as only a narrow liquid-permeable area remains between the inwardly folded side edges.

One way of reducing the risk of edge leakage caused by deformation of the article during use is to provide the article with a preformed raised portion, which during use is intended to lie against the genitalia of the user. In this way, excreted body fluid can be collected as soon as it leaves the body of the user and can be immediately absorbed into the article without running out over its surface.

However, a problem connected with absorbent articles on which a raised portion has been arranged is that the surface which the body fluid meets initially is strictly limited. As a result, during heavy flows of liquid it can occur that all the liquid cannot be immediately absorbed into the raised portion. It is not uncommon for liquid to accumulate between the body of the user and the raised portion. When the user stands up or moves in another way, a gap often occurs between the raised portion and the body of the user. If a large volume of unabsorbed liquid has been enclosed between the body of the user and the surface of the article, this liquid can then flow out through the gap. Such sudden flows of liquid are extremely undesirable as the user perceives them as being uncomfortable and also because they considerably increase the risk of leakage.

Thus, there remains a need for a leakproof absorbent article which works well even for large flows of liquid.

BRIEF DESCRIPTION OF THE INVENTION

An article produced according to the invention, of the type stated in the introduction, is principally characterised in that the raised portion presents spacing elements which, during use of the article, create channels for liquid flow between the raised portion and the body of a user.

The spacing elements can be preformed before use or they can be made in such a way that they do not appear until after wetting.

One way of producing spacing elements which are activated by wetting is by forming a hump with raised portions and thereafter compressing the hump so that it obtains an essentially smooth surface. When the hump is wetted and absorbs liquid, the compressed raised portions will rise up again and form spacing elements on the surface of the hump. Suitable materials for achieving the desired effect are cellulose fluff pulp with high critical bulk, for example chemical thermomechanical cellulose fluff pulp (CTMP), absorbent foam material and other materials that maintain compression before wetting. The compressed structure can be bound with a water-soluble binding agent in order to maintain the compression before wetting.

Providing the raised portion of the article with spacing elements means that the raised portion will not seal against the body of the user. This eliminates the risk of liquid that has not had time to be absorbed by the raised portion being enclosed between the raised portion and the genitalia of the user. Instead, the liquid can run into the channels that are formed between the spacing elements and be absorbed by the side portions of the raised portion or in absorption material arranged at the base of the raised portion.

The spacing elements can be in the form of raised ridges, sunken channels or trenches or of a plurality of projection projecting from the raised portion. These projections can have any suitable form but, for reasons of comfort, should present a rounded surface towards the user of the article. If the spacing elements are in the form of ridges or channels, these should preferably extend principally in the transverse direction of the article. Accordingly, a raised portion can present both raised ridges and sunken channels, or both ridges and projections, etc.

The spacing elements can be formed integrally with the raised portion or they can consist of strips, bands or the like of absorbent or non-absorbent material which has been applied to the raised portion. The spacing elements can be part of a forming element which gives form stability to the raised portion.

It is an advantage if the raised portion is shape stable in both wet and dry conditions, since it is thus possible in each situation to predict the form of the raised portion. Being shape stable implies that the raised portion during normal use will remain essentially unaffected and will not be deformed when it is subjected to pressure and shearing forces arising during used. Furthermore, the shape of the raised portion should not be appreciably altered during absorption of body fluid. An absorbent article with a raised portion which resists deformation when subjected to pressure during use is described in PCT/SE97/01886. Further, absorbent materials that have essentially the same volume in wet and dry conditions are described in PCT/SE97/01883.

Another way to achieve a shape stable raised portion is when the raised portion comprises a forming element. Such a forming element advantageously comprises a rigid plastic material.

According to one embodiment of the invention, raised edge barriers are arranged along the side edges of the article.

According to another embodiment, a camouflage layer is arranged between the liquid-permeable cover layer and the spacing elements on the raised portion in order to conceal the spacing elements. Such a camouflage layer can be a very porous fibre layer which does not hinder the flow of liquid in the channels between the spacing elements. Alternatively, the camouflage layer can be formed of material which collapses when wetted, whereby the raised portion of the article during and after use has a relief structure that is observable from the surface.

Examples of materials which can be used to camouflage the spacing elements are fibres of viscose, cotton, hydrophilicised polypropylene, or mixtures thereof.

To prevent the raised portion from causing discomfort in the form of chafing or pressure during use, but nevertheless to provide good body contact so that excreted body fluid can be collected as soon as it leaves the body of the user, it is essential that the raised portion is given an anatomically correct form. A hard, shape stable hump, which essentially is not affected by the forces occurring during use, should not, accordingly, be so high that it presses against the body of the user and thus causes discomfort during use. Further, it is necessary to ensure that the raised portion does not chafe the sensitive soft parts in the crotch of the user. If has been shown that a raised portion which at its highest part projects at least 5 mm, but not more than 20 mm, from the surface of the article fulfills the requirements of both good body contact and high user comfort.

Correspondingly, a shape stable hump should be relatively narrow, suitably between 2 mm and 25 mm at the base and preferably between 12 mm and 16 mm. The hump is suitably formed with a principally triangular cross section and, accordingly, it is broader at the base than at the top. As the hump is relatively narrow, it can, without discomfort to the user, project in somewhat between the labia of the user. It is an advantage if the hump parts the labia somewhat as this facilitates the transfer of liquid from the user to the article.

The raised portion should have such a form at its rear part that it lies in close contact against the body of the user in the area behind the vaginal opening. Body fluid is thus prevented from running backwards in the furrow between the buttocks of the user and leaking out of the article. Such backward leakage is especially troublesome when the user is lying down. In a corresponding manner, the front part of the raised portion should connect against the body shape of the user in the area in front of the vaginal opening.

In order to connect against the anatomy of the user, the raised portion should be highest at that part of the article which is intended to lie against the vaginal opening of the user. From the highest part, the height should gradually decrease in a direction towards the end portions of the article. The raised portion should extend backwards from the highest part between 5 mm and 40 mm and preferably between 10 mm and 30 mm. In front of the highest part, the raised portion should have a length of between 30 mm and 90 mm, preferably between 55 mm and 80 mm. The raised portion suitably has a total length which is between 40 mm and 140 mm in the longitudinal direction of the article and preferably between 70 mm and 120 mm.

A raised edge barrier can advantageously be arranged on both sides of the central raised portion. The edge barriers increase the leakage security of the article by serving as seals against the groin of the user. Raised edge barriers can be produced in a number of different ways. Examples of commonly occurring side barriers are elastic side edges, foam rubber strips, wadding or the like. Edge barriers can either be purely physical barriers or can prevent the passage of liquid by absorbing body fluid.

BRIEF DESCRIPTION OF THE FIGURES

The invention will be described below in more detail, with reference to the figures shown in the attached drawings, in which.

DESCRIPTION OF EMBODIMENTS

Figure 1:
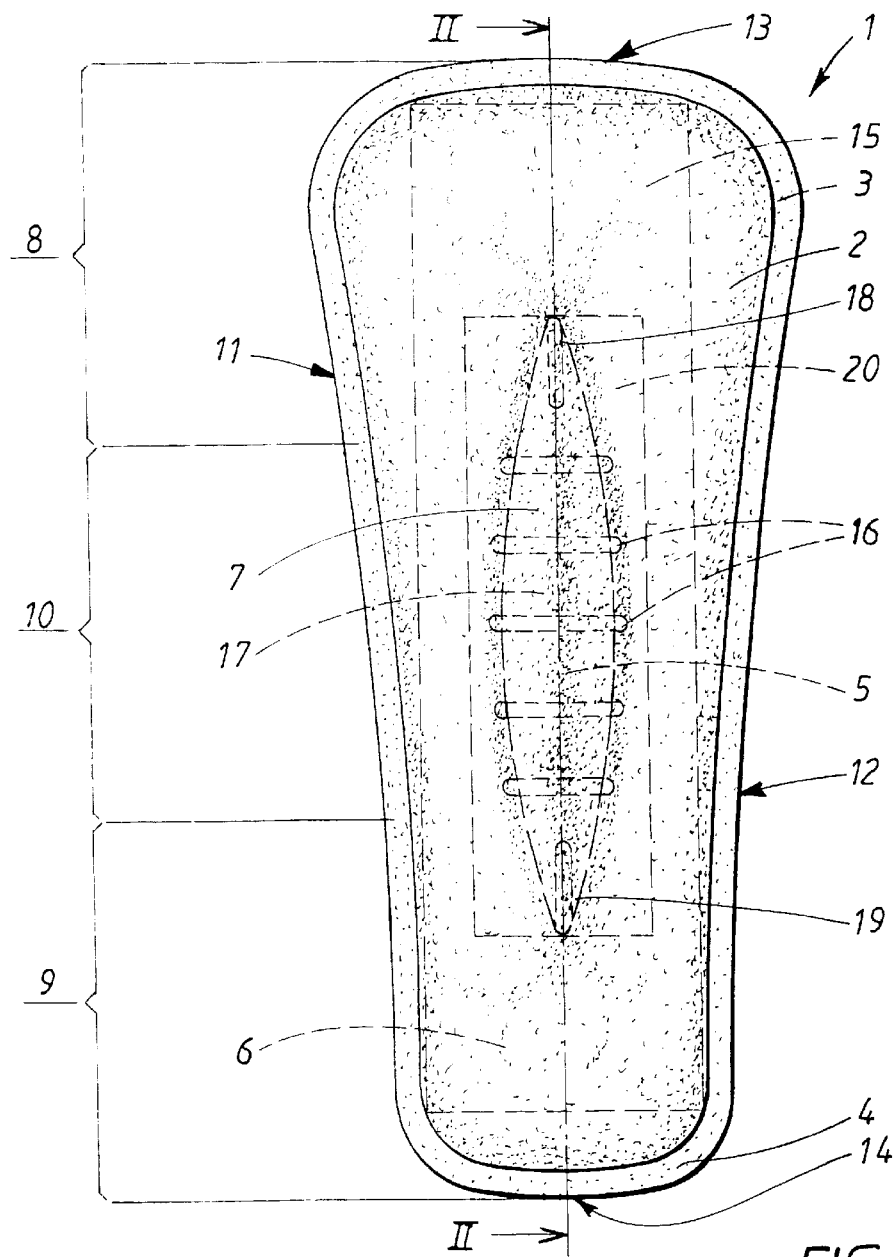
FIG. 1 shows a plan view of a sanitary napkin in accordance with the invention, seen from the side which faces towards the user during use.
Figure 2:
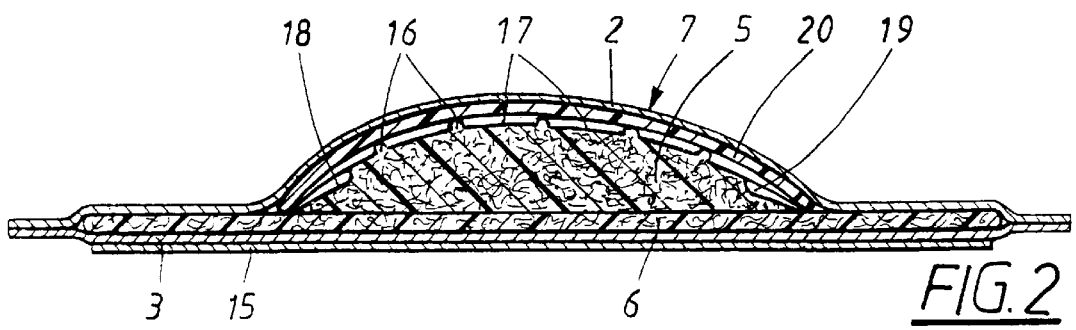
FIG. 2 shows a longitudinal section along the line ll—11 through the sanitary napkin in FIG. 1.

The sanitary napkin 1 shown in FIGS. 1 and 2 comprises a liquid-permeable cover layer 2 arranged on the side of the sanitary napkin 1 which is intended to face toward the user during use. The liquid-permeable cover layer 2 suitably consists of a soft, skin-friendly material. Examples of liquid-permeable cover materials that can be used are different types of unwoven fibre fabrics, known as nonwoven materials. Other existing liquid-permeable cover materials are perforated plastic films, net, knitted, crocheted or woven textiles and combinations and laminates of the listed material types.

The sanitary napkin 1 further comprises a liquid-impermeable cover layer 3 arranged on the side of the sanitary napkin 1 that is intended to face away from the user during use. A thin plastic film is commonly used as a liquid-impermeable cover layer 3. However, it is also possible to use liquid-permeable material layers which are coated with liquid-impermeable material.

Other treatments, such as heat-calendering to melt an initially permeable material to a principally liquid-impermeable layer, can also be used. It is also possible to use a nonwoven material, or other textiles which are so dense and the fibres of which are so hydrophobic that they can function as a liquid barrier layer.

The two cover layers 2, 3 are mutually joined and form a projecting joining edge 4 around the periphery of the sanitary napkin. The join between the cover layers 2, 3 can be brought about using any known technique suitable for the purpose, such as gluing, welding, or sewing.

The two cover layers 2, 3 enclose between them a first absorbent body 5, and a second absorbent body 6. The first absorbent body 5 forms an elongate raised portion 7 at the surface of the sanitary napkin that is intended to face towards the user during use.

The second absorbent body 6 is arranged between the first absorbent body 5 and the liquid-impermeable cover layer 3 and has principally the same form as the sanitary napkin in its entirety. One purpose of the second absorbent body 6 is to collect any body fluid that is not absorbed by the first absorbent body 5. Accordingly, in the shown embodiment the second absorbent body 6 is not intended to receive any large quantities of liquid and can therefore be composed of, for example, one or several layers of a suitable absorbent material such as cellulose fluff pulp, absorbent nonwoven, tissue, foam, or the like. Another purpose of the second absorbent body 6 is to give the sanitary napkin a certain stability.

Figure 3:
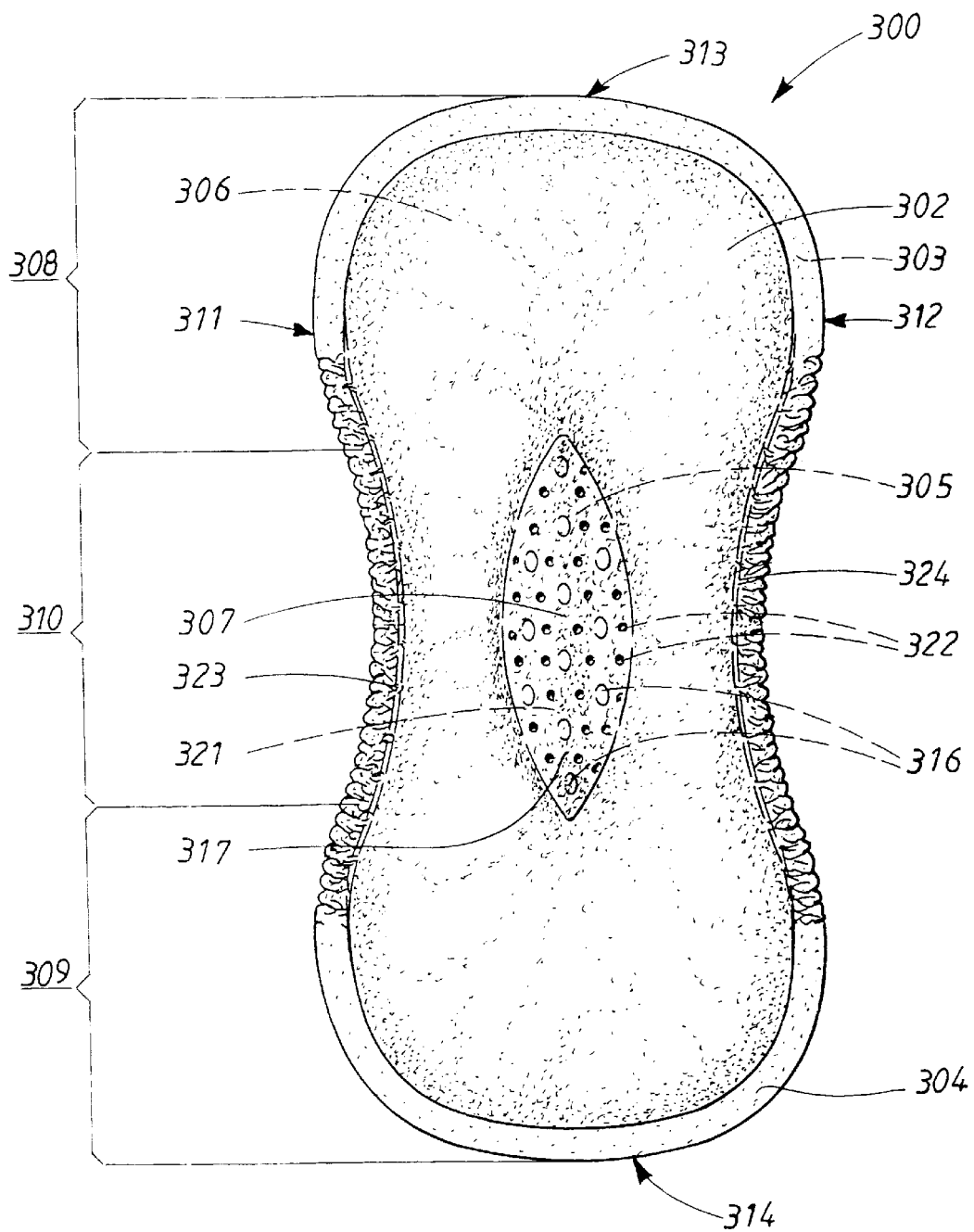
FIG. 3 shows a plan view of a sanitary napkin according to a second embodiment of the invention, seen from the side which faces towards the user during use.
Figure 4:
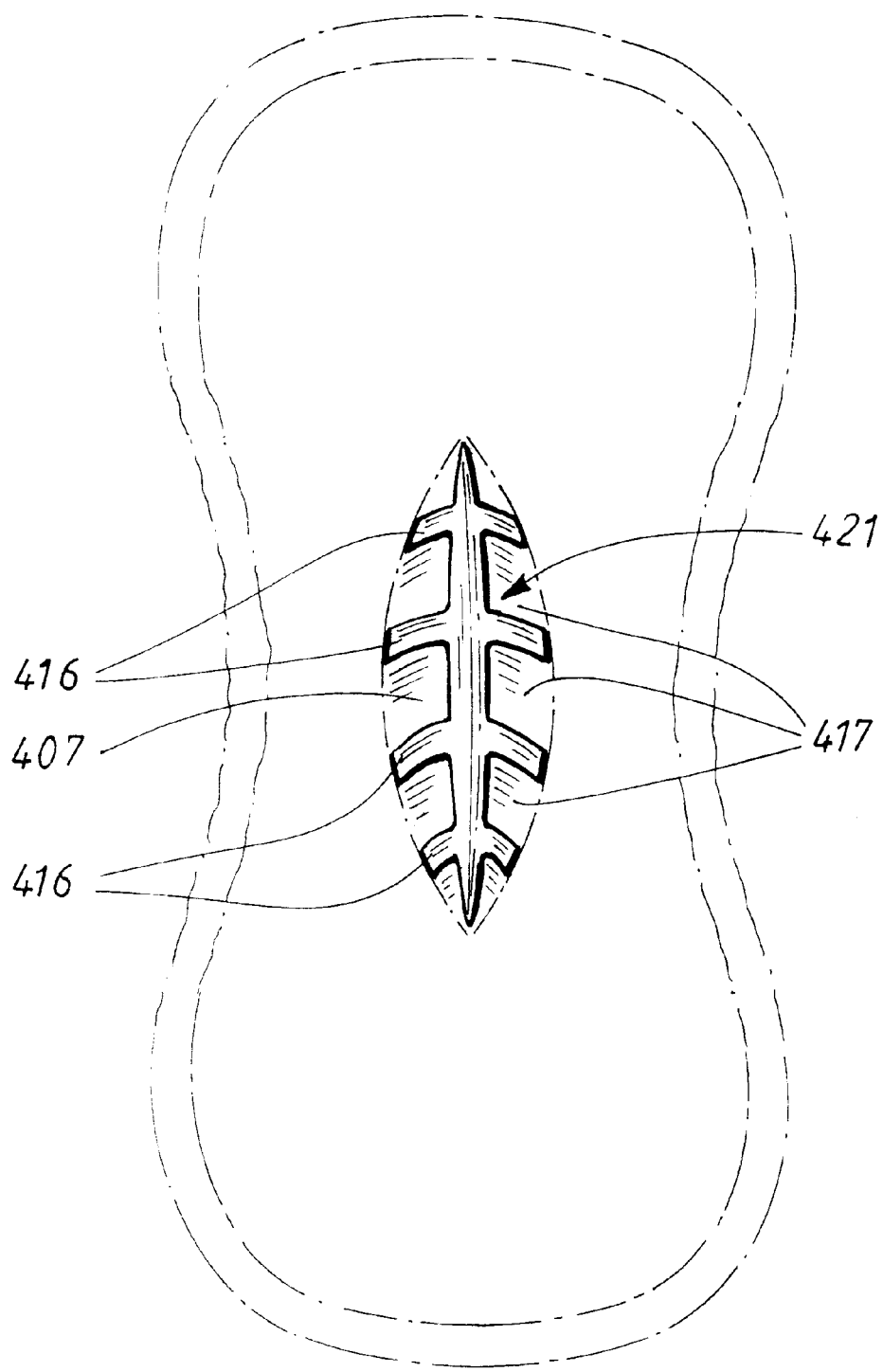
FIG. 4 shows a forming element for stabilising a raised portion, seen from the side which is intended to face towards a user during use.

According to an alternative embodiment, the first absorbent body 5 can be formed of material that receives liquid and transports it to the second absorbent body 6, which in such an embodiment has greater absorption capacity than the first absorbent body 5 and thus can function as the main absorbent body in the sanitary napkin. Suitable materials for the first absorbent body are then fibre materials with low absorption ability but high acquisition ability and liquid-permeability. The second absorbent body can advantageously contain absorbent fibre material, for example cellulose fluff pulp, superabsorbent polymers or the like. In order to attain good shape retention in the raised portion 7, said portion can comprise a shape-stabilising body, for example of the type described in PCT/SE97/1884. Other types of shape-stabilising bodies can of course also be used. Examples of further embodiments of shape-stabilising bodies are shown in FIGS. 3 and 4.

The sanitary napkin 1 has a trapezial form with a broader front portion 8, a narrower rear portion 9 and an intermediate crotch portion 10. The sanitary napkin 1 further displays two longitudinal side edges 11, 12 and two end edges 13, 14. The longitudinal raised portion 7 is broadest and highest at the crotch portion 10 of the sanitary napkin and becomes narrower towards the front portion 8 and the rear portion 9, respectively.

An attachment member 15 in the form of a longitudinal rectangular area of self-adhesive glue is arranged on the surface of the liquid-impermeable cover layer 3 that faces away from the user. The attachment member 15 extends over the major part of the surface of the liquid impermeable cover layer 3 between the two end edges 13, 14. It is, of course, possible to use other glue patterns, such as longitudinal stripes, transverse areas, dots, circles, or other figures. Neither is the invention limited to adhesive attachment bodies; friction attachments and other types of mechanical attachment devices, such as press studs, clips, girdles, pants or the like can be used if this is found to be appropriate.

The first absorbent body 5 forms, as stated, a central raised portion 7. Due to the form of the sanitary napkin with the central raised portion 7, the sanitary napkin is kept in contact with the body of the user during use. The liquid that is excreted is therefore immediately collected by the raised portion 7 and can be absorbed by the first absorbent body 5. As the first absorbent body 5 is intended to receive and absorb almost all emitted body fluid, the absorption capacity of the first absorbent body 5 should correspond to the total amount of liquid that the sanitary napkin is estimated to absorb during use.

However, it can occur that a large amount of liquid is emitted during a relatively short space of time and the absorption speed in the first absorbent body 5 is not sufficient for all the liquid to be immediately absorbed in through the relatively small surface of the raised portion 7 which is initially wetted by the liquid. In order to prevent liquid from gathering between the body of the user and the raised portion 7, the raised portion 7 is therefore provided with spacing elements 16 in the form of transverse raised ridges, which between themselves define channels 17 for collection and transport of excess liquid. Moreover, a sunken channel 18, 19 is arranged at each end of the raised portion.

The first absorbent body 5 is preferably formed of a material which does not collapse during use and which preferably retains its shape even after wetting. The fibre materials described in WO 94/10953 and WO 94/10956 are examples of suitable absorbent materials. These materials have high absorption capacity and a high ability to withstand deformation during use. Other materials that can be used are various types of foam, conventional cellulose fluff pulp, fibre wadding or the like. Furthermore, the first absorbent body 5 can comprise highly absorbent polymer material, usually called superabsorbents. Various combinations of materials can also be used. The material combinations described in PCT/SE97/01883 are particularly suitable.

The spacing elements 16 can be visually perceived as uncomfortable or can give the sanitary napkin a less attractive appearance. The sanitary napkin shown in FIGS. 1 and 2 is therefore provided with a camouflage layer 20, which is arranged between the first absorbent body 5 and the liquid-permeable cover layer 2. The camouflage layer 20 suitably consists of a porous wadding layer or loose fibres which collapse when wetted.

Before use of the sanitary napkin, the camouflaged hump 7 displays an essentially smooth surface. When the raised portion 7 is wetted by body fluid the camouflage layer 20 collapses, whereupon the channels 17 between the spacing elements 16 and the front and rear channels 18, 19 in the raised portion are activated to receive and transport temporary heavier flows of liquid. Examples of materials which have been found to be suitable as camouflage layers are hydrophilic fibres such as viscose, cotton, cellulose fluff, hydrophilicised polypropylene fibres or various types of mixtures. Soft, compressible fibre layers which have large pores and can quickly let liquid through, but which do not necessarily collapse on wetting can also be used. The camouflage layer 20 is not critical to the invention and can be excluded.

A further example of a sanitary napkin 300 in accordance with the invention is shown in FIG. 3. The sanitary napkin 300 is composed of a liquid-permeable cover layer 302, a liquid-impermeable cover layer 303 and an absorbent body composed of two parts 305, 306 enclosed between the cover layers 302, 303. A first absorbent body 305 forms a raised portion 307 on the side of the sanitary napkin 300 that is intended to face towards the user during use. A second absorbent body 306 is arranged between the first absorbent body 305 and the liquid-impermeable cover layer 303 and is intended to receive excess liquid which may run on the outside of the first absorbent body 305.

The sanitary napkin 300 is hourglass-shaped, with broader end portions 308, 309 and a narrower central portion 310 and displays longitudinal side edges 311, 312 and transverse end edges 313, 314.

In order to achieve shape stability in the raised portion 307, a first absorbent body 305 is arranged inside a rigid shell 321, for example of plastic. The shell is formed with a plurality of projecting spacing elements 316 in the form of knobs with a rounded surface, which between themselves define channels 317 for liquid flow. To allow liquid to pass in to the absorbent body 306 within the shell 321, this is provided with a plurality of perforations 322. In FIG. 3 the shell 321 projects up through the liquid-permeable cover layer 302. Alternatively, the shell 321 can, of course, be covered by the liquid-permeable cover layer 302.

By using a special stabilising element for the raised portion 307, the first absorbent body 305 can be formed of any absorbent material with suitable absorption qualities, regardless of the shape stability of the material. Accordingly, it is possible to use soft fibre structures of synthetic or natural fibres with or without the addition of superabsorbent material.

Another advantage of forming the raised portion 307 of a liquid-resistant material, such as plastic, is that the raised portion 307 has a well-defined form and size under all conditions of use.

The sanitary napkin shown in FIG. 3 further comprises elastic members 323, 324, which are arranged along the longitudinal side edges 311, 312 of the sanitary napkin. The elastic members 323, 324 are applied in a pre-stretched condition, preferably in the edge joint 304 between the two cover layers 302, 303, for example by gluing or welding. Due to the fact that elastic members 323, 324 pull the material together along the side edges 311, 312 of the sanitary napkin, the sanitary napkin is curved in the longitudinal direction, at the same time as the side edges are raised up to form side leakage barriers. Common types of elastic members for this purpose are threads, bands or the like. Alternatively, the elastic members 323, 324 can be applied on the outside of one of the cover layers 302, 313. The elastic members can then be composed of, for example, elastic bands which are folded around the side edges 311, 312 of the sanitary napkin. As is shown in the Figure, the elastic members 323, 324 extend only over a central part of each side edge 311. 312. Alternatively, it is of course possible to arrange elastic members along the entire or a large part of the side edges.

Although the sanitary napkin shown in FIG. 3 is not provided with a camouflage layer of the type described in connection with the sanitary napkin in FIGS. 1 and 2, it is of course also possible to provide the sanitary napkin in FIG. 3 with such a camouflage layer.

FIG. 4 shows a forming element 421 which can be used to obtain shape stability in a raised portion that does not have sufficient shape stability of its own. The forming element 421 is arranged on that surface of the absorbent article that is intended to face towards the user during use. In order to clearly show the appearance of the forming element, no liquid-permeable cover layer has been drawn in the Figure. However, it is of advantage if such a cover layer is arranged over the forming element 421 and the raised portion 407 lying within. The forming element 421 is suitably formed of a rigid plastic material which has been formed to the appearance shown in FIG. 4. Naturally, other materials, such as card or metal can be used. The shown forming element gives the raised portion 407 stability but, due to the skeleton-like construction of the forming element 421, liquid flow to the raised portion 407 is not prevented to any appreciable extent. In addition, the forming element serves as spacing elements 416 which create channels 417 for the flow of liquid between the raised portion 407 and the body of a user.

The invention has been described above in connection with sanitary napkins. However, it is also possible to utilise the invention for other absorbent articles which are intended to be worn by female users. Accordingly, the invention also includes panty liners and incontinence protectors for women.

What is claimed is:

1. An absorbent article intended for female users, having such a form and size that it can principally be accommodated in a crotch part of a pair of underpants, and having a longitudinal direction, a transverse direction and a thickness direction, the article comprising:

a liquid-permeable layer;

a liquid-impermeable layer;

two longitudinal side edges;

two transverse end edges;

an absorbent core comprising at least one absorbent body arranged between the two layers;

a raised portion extending in the longitudinal direction, having two end parts, and being arranged at the liquid-permeable layer; said raised portion comprising spacing elements; and a plurality of channels located between spacing elements on the raised portion; said channels extending principally in the transverse direction of the article, and permitting liquid flow in a direction towards the side edges of the article.

2. The absorbent article according to claim 1, wherein the spacing elements comprise raised ridges, extending principally in the transverse direction of the article.

3. The absorbent article according to claim 1, further comprising a sunken channel arranged at an end portion of the raised portion, and extending principally in the longitudinal direction of the article.

4. The absorbent article according to claim 1, wherein the spacing elements comprise knobs projecting from the raised portion.

5. The absorbent article according to claim 1, wherein the raised portion comprises a stabilizing element.

6. The absorbent article according to claim 5, wherein the stabilizing element comprises rigid plastic material.

7. The absorbent article according to claim 1, further comprising elastic members arranged along the side edges of the article; said elastic members raising the side edges to form side leakage barriers.

8. The absorbent article according to claim 1, further comprising a camouflage layer arranged between the liquid-permeable layer and the spacing elements on the raised portion.

9. The absorbent article according to claim 8, wherein the camouflage layer comprises hydrophilic fibers which collapse on wetting.

10. The absorbent article according to claim 1, wherein the raised portion is between 40 mm and 140 mm in the longitudinal direction of the article.

11. The absorbent article according to claim 1, wherein the raised portion is between 70 mm and 120 mm in the longitudinal direction of the article.

* * * * *